US009824183B1

(12) United States Patent
Gupta et al.

(10) Patent No.: US 9,824,183 B1
(45) Date of Patent: Nov. 21, 2017

(54) AUGMENTATION AND PROCESSING OF DIGITAL INFORMATION SETS USING PROXY DATA

(75) Inventors: Neeraj Gupta, Austin, TX (US); Thomas E. Rowe, Austin, TX (US); Ryan A. Cush, Austin, TX (US); Kevin Brannon, Austin, TX (US); Rohit M. Namjoshi, Austin, TX (US)

(73) Assignee: Versata Development Group, Inc., Austin, TX (US)

(*) Notice: Subject to any disclaimer, the term of this patent is extended or adjusted under 35 U.S.C. 154(b) by 2160 days.

(21) Appl. No.: 11/127,875

(22) Filed: May 12, 2005

(51) Int. Cl.
*G06Q 50/22* (2012.01)
*G06F 19/00* (2011.01)
*G06F 17/24* (2006.01)

(52) U.S. Cl.
CPC .......... *G06F 19/322* (2013.01); *G06F 17/243* (2013.01); *G06Q 50/22* (2013.01)

(58) Field of Classification Search
CPC ...... G06C 50/22; G06F 17/243; G06F 19/322
USPC .......................................... 705/2–3; 703/2–3
See application file for complete search history.

(56) References Cited

U.S. PATENT DOCUMENTS

| 5,515,524 A | 5/1996 | Lynch et al. |
| 5,550,746 A | 8/1996 | Jacobs |
| 5,655,085 A | 8/1997 | Ryan et al. |
| 5,668,995 A | 9/1997 | Bhat |
| 5,708,798 A | 1/1998 | Lynch et al. |
| 5,825,651 A | 10/1998 | Gupta et al. |
| 5,940,812 A | 8/1999 | Tengel et al. |
| 6,002,854 A | 12/1999 | Lynch et al. |
| 6,052,669 A | 4/2000 | Smith et al. |
| 6,085,165 A | 7/2000 | Ulwick |
| 6,272,390 B1 | 8/2001 | Skovgaard |
| 6,272,528 B1 | 8/2001 | Cullen et al. |
| 6,405,308 B1 | 6/2002 | Gupta et al. |
| 6,430,730 B1 | 8/2002 | Ghatate et al. |
| 6,578,141 B2 | 6/2003 | Kelley et al. |
| 6,594,635 B1 | 7/2003 | Erlanger |
| 6,654,726 B1 | 11/2003 | Hanzek |

(Continued)

OTHER PUBLICATIONS

Tiihonen, Juha et al., "Modeling Configurable Product Families," 4th WDK Workshop on Product Structuring, Oct. 22-23, 1998, h!!Q://www.soberit.hut.fi/gdmgfnagers/TLSP98.PDF, 22 pages.

*Primary Examiner* — Joy Chng
(74) *Attorney, Agent, or Firm* — Terrile, Cannatti, Chambers & Holland, LLP; Kent B. Chambers

(57) ABSTRACT

A proxy data augmentation system and method intelligently augments digital information sets with proxy data using analytical processing technology. The proxy data system and method identifies fields in a digital information set that are candidates for modification using proxy data. After identifying a candidate field, an analytical process is invoked to evaluate a context of the candidate field. In one embodiment, once the context and at least one other parameter associated with the digital information set are evaluated, the proxy data augmentation system and method can determine appropriate proxy data to populate the candidate field and modify the digital information set with the determined proxy data. The modified document can then be sent to a recipient data processing system. Additionally, the digital information set submitting and/or recipient data processing system can be notified of the existence and identification of the proxy data.

86 Claims, 9 Drawing Sheets

(56) References Cited

U.S. PATENT DOCUMENTS

| | | | |
|---|---|---|---|
| 6,675,294 B1 | 1/2004 | Gupta et al. | |
| 6,684,189 B1 | 1/2004 | Ryan et al. | |
| 6,718,535 B1 | 4/2004 | Underwood | |
| 6,895,388 B1 | 5/2005 | Smith | |
| 7,043,407 B2 | 5/2006 | Lynch et al. | |
| 7,225,412 B2* | 5/2007 | Burdick | G06F 17/3056 707/E17.005 |
| 7,337,179 B1 | 2/2008 | Plain | |
| 7,519,549 B1 | 4/2009 | Johnson et al. | |
| 2001/0034849 A1* | 10/2001 | Powers | G06Q 10/107 726/30 |
| 2002/0026373 A1 | 2/2002 | Kamath et al. | |
| 2002/0049767 A1* | 4/2002 | Bennett | G06F 17/21 |
| 2002/0073001 A1 | 6/2002 | Palmer et al. | |
| 2002/0073138 A1 | 6/2002 | Gilbert et al. | |
| 2002/0087432 A1 | 7/2002 | Muniz | |
| 2002/0111835 A1 | 8/2002 | Hele et al. | |
| 2002/0116231 A1 | 8/2002 | Hele et al. | |
| 2002/0120474 A1 | 8/2002 | Hele et al. | |
| 2002/0143653 A1 | 10/2002 | DiLena et al. | |
| 2002/0165701 A1 | 11/2002 | Lichtenberg et al. | |
| 2002/0174081 A1 | 11/2002 | Charbonneau et al. | |
| 2003/0069754 A1* | 4/2003 | Weeks, Jr. | G06F 19/3418 705/2 |
| 2003/0074277 A1 | 4/2003 | Foutz | |
| 2003/0125997 A1 | 7/2003 | Stoltz | |
| 2004/0010459 A1* | 1/2004 | Zatlukal | G06Q 40/06 705/36 R |
| 2004/0012634 A1 | 1/2004 | Kraemer et al. | |
| 2004/0143464 A1 | 7/2004 | Houle et al. | |
| 2004/0172310 A1 | 9/2004 | Atlee et al. | |
| 2004/0186755 A1 | 9/2004 | Roche | |
| 2005/0028046 A1* | 2/2005 | McArdle | G06F 17/30303 714/48 |
| 2005/0071146 A1 | 3/2005 | Kind | |
| 2005/0102199 A1 | 5/2005 | Lee | |
| 2005/0197926 A1 | 9/2005 | Chinnappan et al. | |
| 2005/0257148 A1* | 11/2005 | Goodman | G06F 17/243 715/226 |

* cited by examiner

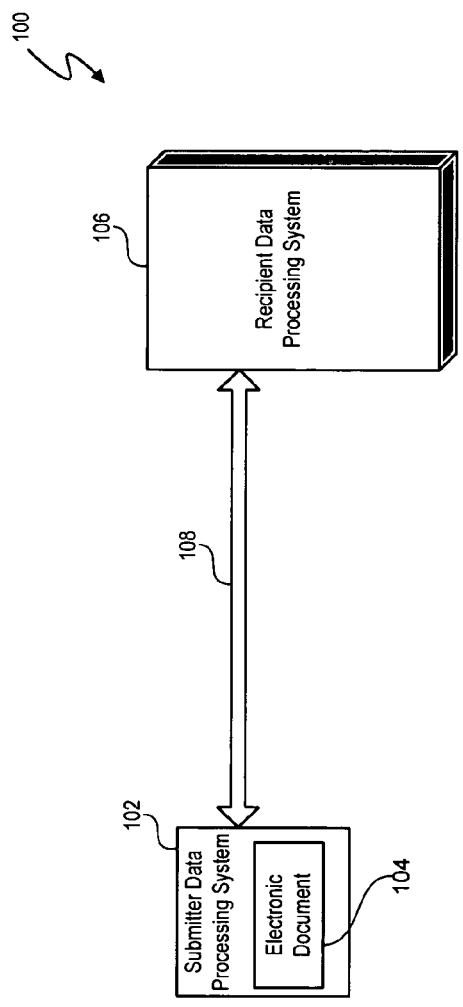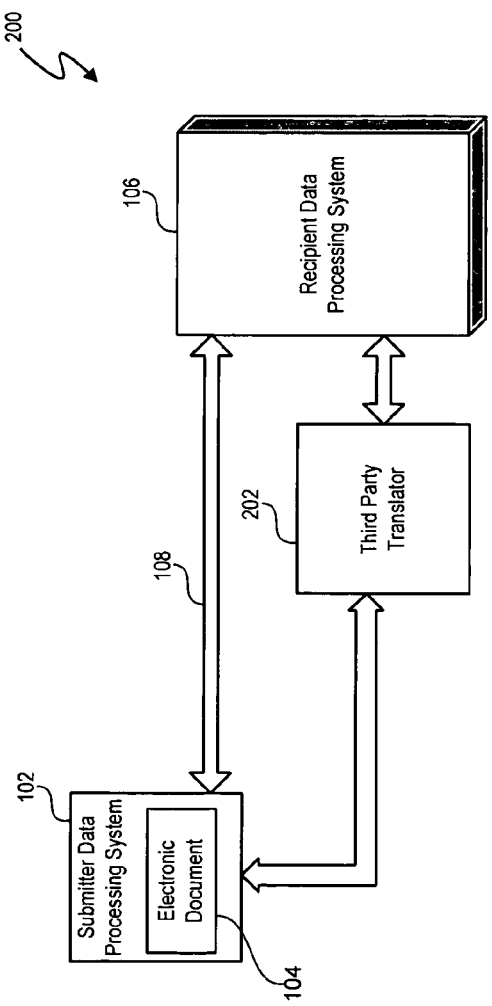
Figure 1 (prior art)
Figure 2 (prior art)

| Cust# | Customer Name | Type | ExpDate | Co | Expiring Premium | Matched Premium | Difference | Matched Carrier | Matched Response |
|---|---|---|---|---|---|---|---|---|---|
| KYLEA-1 | Kylea Inc(see remarks) | WCCO | 09/01/2004 | GCI | $1,150 | $1,093 | $157 | Carrier ABC | Carrier Interested |
| ITASC-2 | Itasca Bancorp, Inc. | WCCO | 09/01/2004 | FED | $14,353 | $12,098 | $2,255 | Carrier XYZ | Carrier Interested |
| CARPE-3 | Carpetland USA | WCCO | 09/01/2004 | GCI | $6,158 | $5,032 | $1,126 | Carrier ABC | Carrier Interested |
| HAWKE-1 | Hawkere Construction Inc | WCAR | 09/05/2004 | TIA | $750 | | | | Not enough data |
| DENTA-1 | Dental Health Associates of IL | WCCO | 09/06/2004 | GCI | $17,838 | $14,309 | $3,529 | Carrier XYZ | Carrier Interested |
| MIXED-1 | Mixed Media Group, Inc. Mixed | WCCO | 09/07/2004 | GCI | $798 | $835 | -$37 | Carrier XYZ | Carrier Interested |
| CODYG-2 | Cody Grinding LLC | WCAR | 09/07/2004 | CSC | $4,814 | $4,015 | $799 | InsureVianet | Carrier Interested |
| MORAN-1 | Moran Services Inc. | WCAR | 09/12/2004 | CSC | $750 | | | InsureVianet | Not enough data |

Agency RADAR Response to Analyzed Policies

Carrier Interested: 12 policies
Not Enough Data To Determine Interest: 9 policies
No response from server: 1 policies
No Carrier Interested: 2 policies
Total Policies Analyzed: 24

AUGMENTATION AND PROCESSING OF DIGITAL INFORMATION SETS USING PROXY DATA

CROSS-REFERENCE TO RELATED APPLICATION

This application claims priority under 35 U.S.C. §120 to the following commonly assigned U.S. patent applications, which provide example methods and apparatus and are all hereby incorporated by reference in their entireties:
a. U.S. patent application Ser. No. 10/987,337 entitled "Matching of Agency Customer Product Data with Underwriting Criteria", inventors Neeraj Gupta, Thomas E. Rowe, Ryan A. Cush, Kevin Brannon, and Rohit M. Namjoshi;
b. U.S. patent application Ser. No. 10/987,090, and entitled "System and Method for Providing an Early Indication of a Degree of fit Between Underwriting Criteria and Underwritten Product Data", inventors Neeraj Gupta, Ryan A. Cush, Thomas E. Rowe, Kevin Brannon, and Rohit M. Namjoshi; and
c. U.S. patent application Ser. No. 10/987,329, and entitled "Matching and Prioritizing Underwriting Related Data with Underwriting Criteria", inventors Neeraj Gupta, Thomas E. Rowe, Ryan A. Cush, Kevin Brannon, and Rohit M. Namjoshi.

BACKGROUND OF THE INVENTION

Field of the Invention

The present invention relates in general to the field of information processing, and more specifically to a system and method for automatically and intelligently augmenting and processing digital information sets, such as electronic documents, using proxy data.

Description of the Related Art

Many businesses, organizations, and other entities allow and often prefer individuals and other entities to submit information electronically using electronic documents, such as electronic forms. Individuals utilize computers to submit electronic documents to order products, request quotes for products, make applications to an organization, and for a myriad of other purposes. Computer software applications themselves can also be utilized to submit electronic documents on behalf of an individual or other entity.

FIGS. 1 and 2 depict networked systems 100 and 200 for submitting electronic documents. A user of the submitter data processing system 102 uses a computer executable program, such as a web browser application or specialized data entry program, to display electronic document 104. The electronic document can be a web page or other document used by a user of data processing system 102 to enter data into the data processing system 102. The electronic document can be any kind of electronic document such as word processing document, a spread sheet document, or an extensible markup language document. The data processing system 102 stores the electronic document as a file, as a string of bits, or as any other electronic representation. The data processing system 102 may store the electronic document in temporary memory (e.g. system memory) and/or in long-term memory (e.g. on a hard drive). The electronic document 104 is then submitted to a recipient data processing system 106 via an electronic communication path 108, such as the Internet.

Referring to FIG. 2, in some systems a third party translator 202 receives the electronic document and translates the document into a form useable by the data processing system 106. The translator 202 can be an application executed by data processing system 102, by data processing system 106, or by a third party data processing system. In some systems, the data processing system 106 can provide follow-up communication to data processing 102. For example, data processing system 106 can send a 'document accepted' type message to data processing system 102. In other situations, when the electronic document 102 includes omitted, incomplete, or obviously inaccurate data fields, data processing system 106 may issue a 'document rejection' type method.

Some electronic documents require only information that is readily available to the user, such as name, address, e-mail address, billing information, and an identification of products to be ordered. Completion of such forms by a user is generally very straightforward and easy. Other electronic forms require information to be provided that is much less straightforward and can take 15 minutes, 30 minutes, an hour, or longer to complete. The reasons for the long completion times vary from form to form. Sometimes a large quantity of information required to complete the form increases completion times. Sometimes the information needed to accurately complete the form is not readily available to the user. In this case, the user generally either conducts research to obtain the correct information, or the user guesses at the information to be entered.

Completion of forms for underwritten products such as insurance policies (including applications therefore) and financial products, such as mortgages and other financing instruments, provide an example of the time and complexity that can be involved in a form completion and submittal process. Agents complete and submit an electronic form to one or more underwriters to obtain a quote for a particular underwritten product. Given the multitude of available underwritten products and the multitude of underwriters, the number and complexity of forms related to the purchase or obtaining a quote from an underwriter remains a significant obstacle for better efficiency among users that transact business with underwriters. The term "agent" includes agents, customer service representatives (CSRs), agency representatives, and others acting on behalf of others or as intermediaries, an individual acting on behalf of himself/herself, and an entity acting on behalf of itself.

SUMMARY OF THE INVENTION

In one embodiment of the present invention, a data processing system for determining and including contextual proxy data in a digital information set includes a processor and a memory coupled to the processor. The memory includes processor executable code embodied therein to cause the processor to identify a field associated with the digital information set whose content is a candidate for proxy data. The memory also includes processor executable code embodied therein to cause the processor to invoke a process to evaluate a context of the field and evaluate at least one other parameter associated with the digital information set to determine appropriate proxy data with which to populate the field and modify the digital information set with proxy data determined by the process.

In one embodiment of the present invention, a computer readable program product having processor executable code embodied therein to cause a processor to identify a field associated with a digital information set whose content is a candidate for proxy data. The computer readable program product also includes processor executable code embodied therein to cause a processor to invoke a process to evaluate a context of the field and evaluate at least one other parameter associated with the digital information set to determine appropriate proxy data with which to populate the field and modify the digital information set with proxy data determined by the process.

In one embodiment of the present invention, a method for determining and including contextual proxy data in a digital information set includes executing an application in a data processing system for identifying a field associated with the digital information set whose content is a candidate for proxy data, invoking a process to evaluate a context of the field and evaluate at least one other parameter associated with the digital information set to determine appropriate proxy data with which to populate the field, and modifying the digital information set with proxy data determined by the process.

In one embodiment of the present invention, an apparatus method for determining and including contextual proxy data in a digital information set includes means for identifying a field associated with the digital information set whose content is a candidate for proxy data. The apparatus further includes means for invoking a process to evaluate a context of the field and evaluate at least one other parameter associated with the digital information set to determine appropriate proxy data with which to populate the field and means for modifying the digital information set with proxy data determined by the process.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

FIG. 1 (labeled prior art) depicts a system for receiving and submitting digital information sets.

FIG. 2 (labeled prior art) depicts a system for receiving and submitting digital information sets that includes a third party translator.

FIG. 6 depicts a digital information set augmented with proxy data.

FIG. 7 depicts a digital information set augmented with proxy data via interpretation of existing data.

FIG. 8 depicts a digital information set reporting occurrences of proxy data and incomplete data.

DETAILED DESCRIPTION

A proxy data augmentation system and method intelligently augments digital information sets with proxy data using analytical processing technology. The proxy data system and method identifies fields in a digital information set that are candidates for modification using proxy data. After identifying a candidate field, a process is invoked to evaluate a context of the candidate field. In one embodiment, once the context and at least one other parameter associated with the digital information set are evaluated, the proxy data augmentation system and method can determine appropriate proxy data to populate the candidate field and modify the digital information set with the determined proxy data. The modified document can then be sent to a recipient data processing system. Additionally, the digital information set submitting and/or recipient data processing system can be notified of the existence and identification of the proxy data. The proxy data augmentation system and method can, for example, be implemented as an application resident on a data processing system that originates the digital information set or implemented on an intermediate data processing system.

Figure 3:
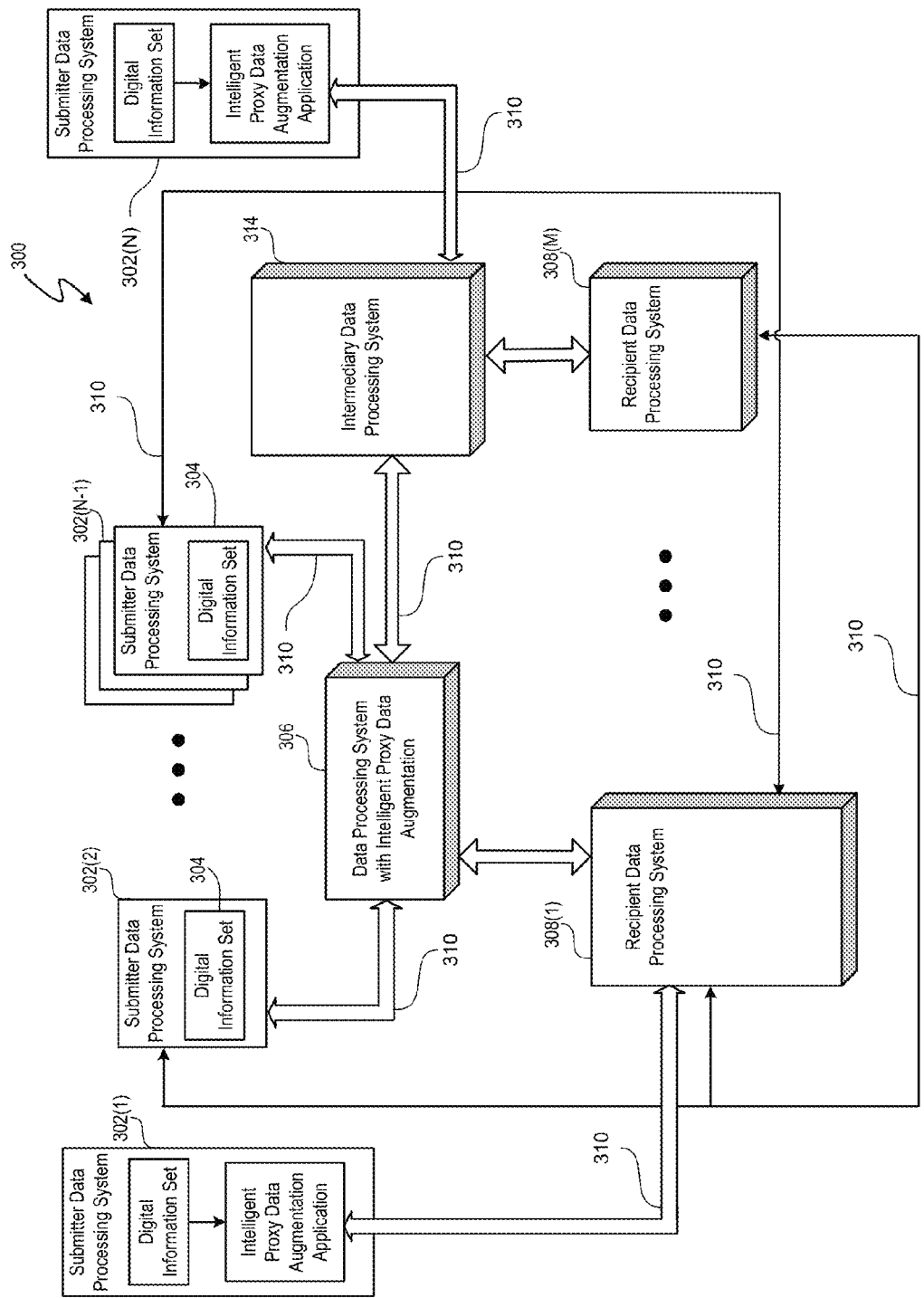
FIG. 3 depicts a system for intelligently augmenting digital information sets with proxy data using analytical processing technology.

FIG. 3 depicts a system for intelligently augmenting digital information sets ("DIS's") with proxy data using analytical processing technology 300 (referred to herein as the "proxy data augmentation system 300"). The proxy data augmentation system 300 includes N submitter data processing systems 302(1) through 302(N), where N is the number submitter data processing systems including groups of submitter data processing systems. 'Data processing systems' is a general term that includes desktop computer systems, notebook computer systems, hand held processing systems, and other electronic/software systems that process data. The submitter data processing systems 302(1)-302(N) (collectively referred to as "submitter data processing systems 302") can be an individual data processing system or a collection of data processing systems interconnected through a network, such as a local area network. The term "submitter" is used to identify the system that submits a DIS 304. The submitted DIS 304 can be immediately sent or stored for subsequent sending. The submitter data processing system generally originates the digital information set. DIS's 304 can represent any kind and number of digital information sets. The DIS's 304(1)-304(N) (collectively referred to as "DIS's 304") can be any kind of digital information set such as an electronic document, an electronic form, data in a database collectively representing a set of information, an electronic spreadsheet, or any digital set of data intended to communicate knowledge or other information.

The embodiment of proxy data augmentation system 300 depicted in FIG. 3 represents a collection of various configurations of submitter data processing systems 302. The submitter data processing system 302(1) represents a single data processing system operated by a user. The user, such as a person or a software application, generates DIS 304(1). Generation of DIS 304(1) can occur in any number of ways. For example, the user could insert data into a user interface that stores the data in one or more tables in a database. In another embodiment, the user could insert data into a word processor document, spread sheet, hypertext markup language ("HTML") document, extensible markup language ("XML") document, or other type of digital document or file (collectively referred to as a "digital document"). The digital document then represents a set of digital information that can be submitted for immediate sending or stored for subsequent submission. The submitter data processing system 302(1) includes an intelligent proxy data augmentation application 306. As described in more detail below, the intelligent proxy data augmentation application 306 identifies one or more candidate fields in DIS 304(1) for augmentation with proxy data, determines the proxy data appropriate for each candidate field, and modifies the DIS 304(1)

with the determined proxy data. A "field" in DIS's 304 represents an occurrence of data or a known absence of data. For example, data representing a person's name, street address, city name, and state name represent exemplary fields of data. If a DIS is missing a "name", and it is known that the DIS should contain data representing a "name", then the "name" field either contains a null value or is missing altogether. The submitter data processing system 302(1) subsequently sends the proxy data augmented DIS 304(1) to one or more recipient data processing systems 308(1)-308(M) such as recipient data processing system 308(1), or to an intermediary data processing system 314, wherein M represents a number of recipient data processing systems. Submitter data processing system 302(N) is, in one embodiment, functionally identical to submitter data processing system 302(1).

Figure 5:
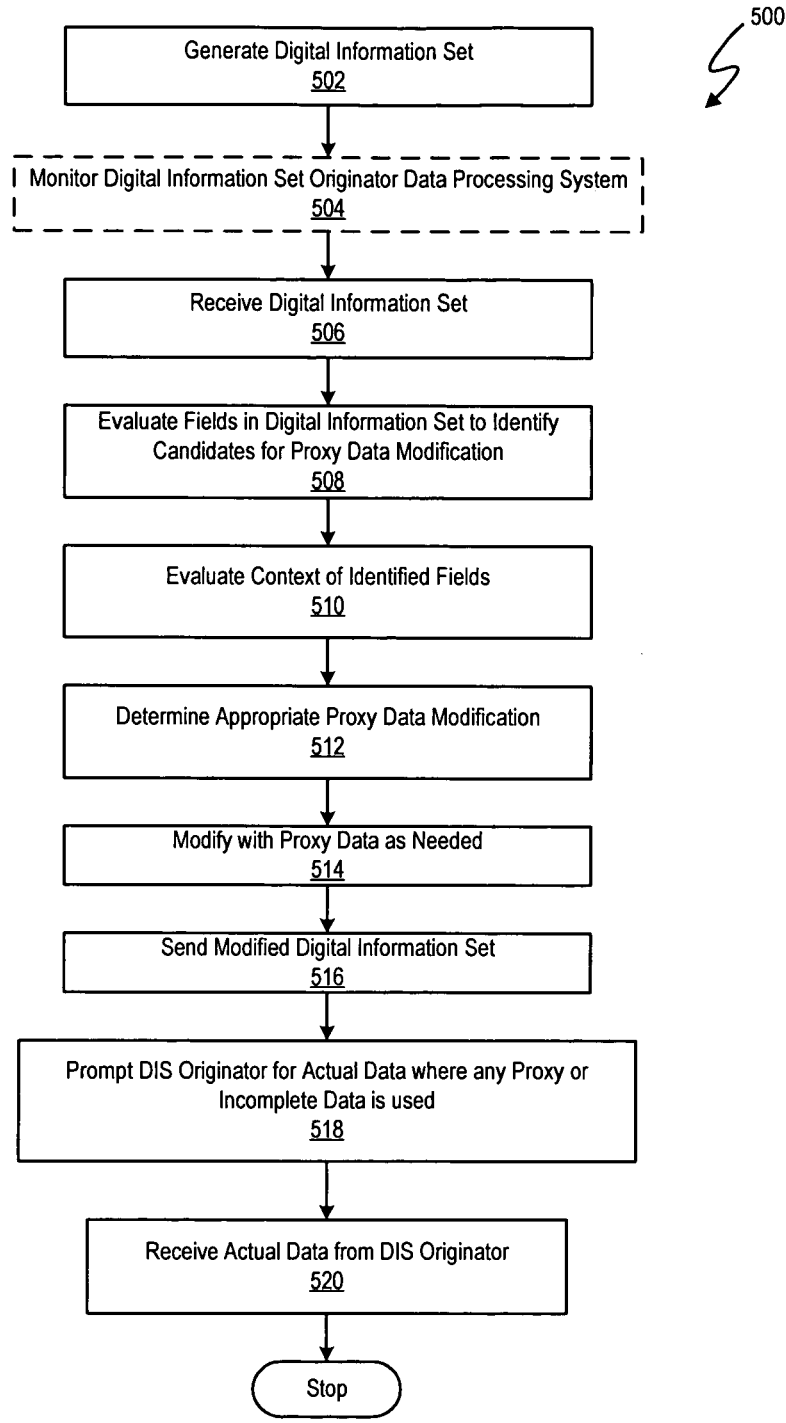
FIG. 5 depicts an intelligent proxy data augmentation process.

In one embodiment, the proxy data augmentation system 300 works in conjunction with intelligent proxy augmentation process 500 depicted in FIG. 5. The submitter data processing systems 302 communicate with other networked data processing systems such as recipient data processing systems 308, data processing system 312, and intermediary data processing system 314 via a communication path 310 such as the Internet. The proxy data augmentation system 300 does not have to modify any application used to create the DIS's 304. Each of submitter data processing systems 302 can send DIS's 304 using any active and/or passive process, such as a manual process, automatically through an automatic send function, or through monitor and interceptor technology. The monitor and interceptor technology represents one embodiment of optional operation 504. An embodiment of monitor and interceptor technology is described in U.S. patent application Ser. No. 10/987,329 with particular reference to the automated interceptor 104 in U.S. patent application Ser. No. 10/987,329 and associated triggering technology. The monitor and interceptor technology in one embodiment represents a passive sending process from the perspective of a submitter data processing system 302(i), which represents the $i^{th}$ data processing system. The monitor and interceptor technology can retrieve sets of data from a database in a submitter data processing system 302(i). The retrieved sets of data each represent a collection of information.

In operation 502, the submitter data processing system 302(2) generates DIS 304(2) and sends the DIS 304(2) to a remotely located data processing system 312. In operation 506, the data processing system 312 receives the submitted digital information set. The data processing system 312 can receive the submitted DIS 304(2) through submitter data processing system 302 sending the DIS 304(2) or by data processing system 312 accessing the data processing system 302 to retrieve the DIS 304(2). The data processing system 312 includes an intelligent proxy data augmentation application that performs the same function as the local version of intelligent proxy data augmentation application 306 installed on submitter data processing system 302(1).

Operations 508, 510, 512, 514, and 516 augment the DIS's 304 with proxy data determined using an analytical process based upon the context of the digital information set. In one embodiment, operations 508, 510, 512, 514, and 516 are performed using proxy data augmentation application 400 and are described in more detail below. In operation 516, after processing a digital information set to augment the document with proxy data, the data processing system 312 sends the proxy data augmented digital information set, for example, either to one or more recipient data processing systems 308 designated by the submitting data processing system 302(i) or to an intermediary data processing system 314.

The intermediary data processing system 314 is generally designated by the intended recipient data processing system 308(i) to process DIS's 304 on behalf of the intended recipient data processing system 308(i), which represents the $i^{th}$ recipient data processing system. The submitter data processing systems 302 can be configured to automatically send DIS's 304 to intermediary data processing system 314. In another embodiment, the intermediary data processing system 314 can be configured to intercept DIS's 304 intended for a recipient data processing system 308(i). In a further embodiment, upon receipt of a digital information set the recipient data processing system 308 can be configured to forward digital information sets to intermediary data processing system 314 for formatting prior to processing by the recipient data processing system 308. The intermediary data processing system 314 generally performs functions such as placing received DIS's 304 into a format acceptable by intended recipient data processing system 308(i). The submitter data processing system 302(1) can also send DIS 304(1) directly to intermediary data processing system 314 if requested to so.

The submitter data processing system 302(N−1) is configured as a group of networked, individual data processing systems. The submitter data processing system 302(N−1) can be linked together into a central system and/or can operate independently of any centralized processing system. As with submitter data processing system 302(2), submitter data processing system 302(N−1) generates a digital information set, DIS 304(N−1), in operation 502 and sends the DIS 304(N−1) to remotely located data processing system 312, which receives the DIS 304(N−1) in operation 506. Operation 504 can also be used to send the DIS 304(N−1) to data processing system 312.

Embodiments of proxy data augmentation system 300 can be configured to include virtually any combination of submitter data processing systems 302, one or more data processing systems 312, and/or one or more intermediary data processing systems 314. In one embodiment, the data processing system 312 receives digital information sets from intermediary data processing system 314, processes the received digital information sets to include proxy data where applicable, and sends the processed digital information sets to the intended recipient data processing system 308(i). In one embodiment, any, some, or all of the submitter data processing systems 302 represent respective insurance industry agent management systems. In one embodiment, any, some, or all of the recipient data processing systems 308 represent data processing systems of insurance carriers or other underwriting type entities. In one embodiment, DIS's 304 are sent, directly or indirectly (e.g. via an intermediary data processing system), to insurance carriers for one or more purposes such as obtaining a non-bindable quote, a bindable quote, an indication if an insurance risk matches the type of risk for which an insurance carrier desires to underwrite (as described in more detail in U.S. patent application Ser. No. 10/987,337).

Figure 4:
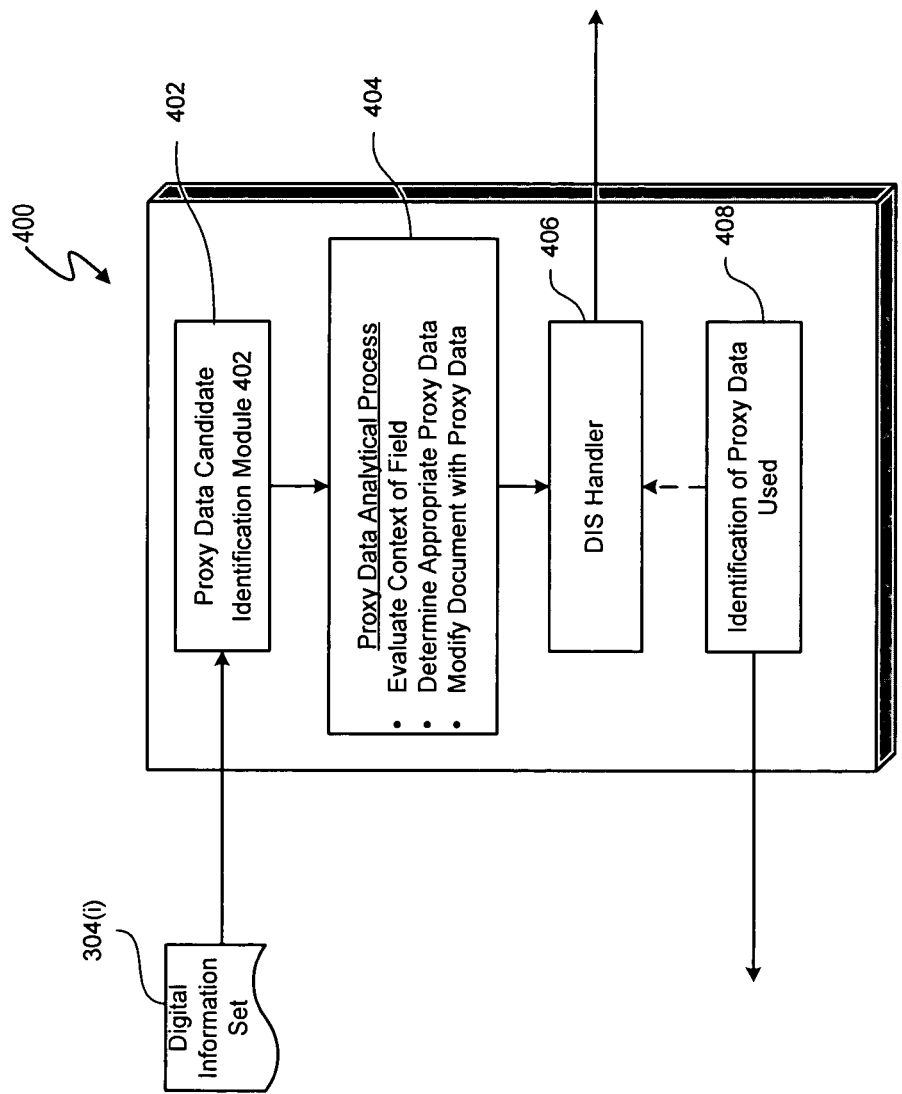
FIG. 4 depicts an intelligent proxy data augmentation application.

FIG. 4 depicts an intelligent proxy data augmentation application 400, which is one embodiment of the intelligent proxy data augmentation application 306 and the intelligent proxy data augmentation application of data processing system 312. The proxy data augmentation application 400 is generally implemented as software code executable by a processor. The code can be stored in a memory, such as a hard drive or a removable medium, such as a compact disk or digital versatile disk. The proxy data augmentation application 400 processes DIS's 304. The DIS 304(i) includes data fields that are intended to contain parameters relevant to the purpose of the DIS 304(i), which represents the i$^{th}$ digital information set. Each DIS 304(i) can also be associated with parameters relevant to the DIS such as the intended recipient of the DIS. The types of data in the data fields of DIS 304(i) depend on the purpose of the DIS 304(i). Particular data fields in a DIS 304(i) or expected to be in a DIS 304(i) are often determined or inferred by the identity of the intended recipient. Thus, the intended recipient often directly or indirectly determines the type of information that a DIS 304(i) should contain. For example, in an insurance context, the data types of data fields DIS 304(i) may include one or more of the data types contained in Tables 1 and 2. Table 1 contains an example list of insurance product related data types and underwriting criteria types. Table 2 contains an example list of additional insurance product related data types used to generate a bindable quote.

TABLE 1

Example List Of Insurance Product Related Data Types And Underwriting criteria Types Agency ID
Postal Code
Effective Date
Employer's Liability
Years in Business
Experience Modification (e-mod)
Deductible (not required for degree of fit determination)
Class Code × Risk
Exposure × Risk
Number of Employees × Risk
Last Year Premium
State
Zip Code

TABLE 2

Example Bindable Quote Data Types

Applicant FEIN
Bureau/Risk ID
Address Line 1
City
Payment Plan
Legal Entity
Additional Locations - Address
Term
AgentID - system log in.
Insured Name The format and data structure of various DIS's 304 may or may not be different. Proxy data augmentation application 400 can be programmed to recognize various data formats and data structures generated by various submitter data processing systems 302. In one embodiment the data formats and data structures are obtained from the intended recipient(s) of DIS's 304. The proxy data augmentation application 400 includes various functional modules to assist in intelligently augmenting the DIS 304(i) with proxy data. The architecture, programming language, and programming techniques used to implement the functionality of intelligent proxy data augmentation application 306 and proxy data augmentation application 400 are a matter of design choice.

The proxy data candidate identification module 402 performs one embodiment of operation 508. In one embodiment, module 402 evaluates the DIS 304(i) and identifies fields that are candidates for proxy data. Candidate fields are, for example, fields that are incomplete, empty, contain information that does not comply with rules that determine accuracy and/or relevancy, or are otherwise determined to be candidates for inclusion of proxy data. Additionally, in some embodiment, the proxy data candidate identification module 402 is programmed to identify all field candidates for proxy data, in other embodiments, proxy data candidate identification module 402 is programmed to recognize a subset of possible proxy data candidates. The subset could, for example, be limited to fields that, if incomplete or inaccurate, would lead to rejection by one of more recipient data processing system 308.

Once proxy data candidate fields are identified, in operation 510 a proxy data analytical process module 404 evaluates the context of the identified candidate field. The context of the candidate field can be determined, for example, by its placement in the digital information set or by a tag that generically identifies the field. For example, a field for specifying the number of employees of a company may be the fifth field in a document or may be labeled with a tag such as [Number of Employees].

In operation 512, once the context of the candidate field is known, proxy data analytical process module 404 can apply appropriate analytical processes to determine the appropriate proxy data with which to populate the candidate field. The proxy data analytical process module 404 generally uses at least one parameter associated with the DIS 304(i) to determine the appropriate proxy data. For example, by reviewing the intended recipient of the DIS 304(i), the proxy data analytical process module 404 can determine appropriate neutral values for the intended recipient data processing system(s) 308. For example, if the DIS 304(i) is an insurance risk application and is missing an "experience modification (e-mod) value" and a "years in business" value, the proxy data analytical process module 404 could modify the e-mod and years in business data fields with proxy data e-mod=1.0 and years in business=9, respectively, if 1.0 and 9 represent neutral values for the intended recipient data processing system(s) 308.

Figure 6:
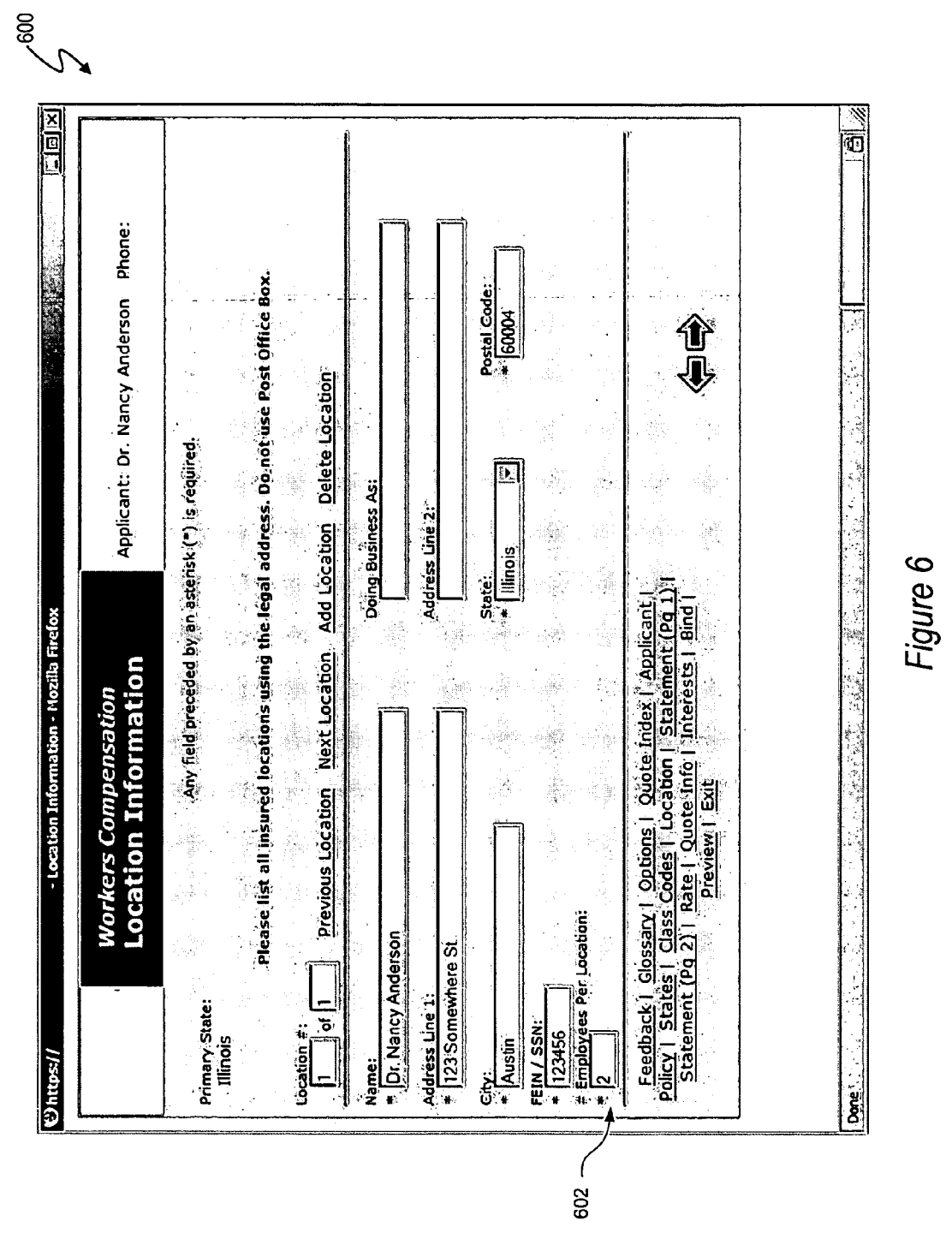

The proxy data analytical process module 404 can also use other parameters in the DIS 304(i) to apply rules which calculate proxy data based on known or estimated relationships between parameters. Referring also to FIG. 6, for example, if a "number of employees value" is missing in a data field, the proxy data analytical process module 404 can modify the number of employees data field with a value determined from an equation such as "number of employees=(Total Payroll)/(Average pay per employee for a particular business class code)." FIG. 6 depicts a user interface 600 from which a DIS 304 can be generated. Based on Total Payroll and Average Pay Per Employee for a Particular Business Class Code as entered by the user elsewhere in the digital information set, the proxy data analytical process module 404 determines that the number of employees at the particular indicated location 602 is two (2).

The proxy data analytical process module 404 can also include rules such as insurance related rules to determine appropriate proxy data. For example, an insurance related rule can be: if a class_code=X, then e-mod<1.3, where X represents a class code value or other representation of the class.

Additionally, the proxy data analytical process module 404 may detect data that is inaccurate based on an evaluation of the data content contained in a field. For example, the data content of a field may be misspelled or clearly misplaced. For example, if the DIS 304(i) detects a field labeled by a user of submitter data processing system 302(i) with "mreit rating", proxy data analytical process module 404 can using logic to deduce that given the context of the digital information set based upon, for example, the intended recipient of the DIS 304(*i*) or based upon an identification of the context included in the DIS 304(*i*), that "mreit rating" should be replaced with "merit rating".

Figure 7:
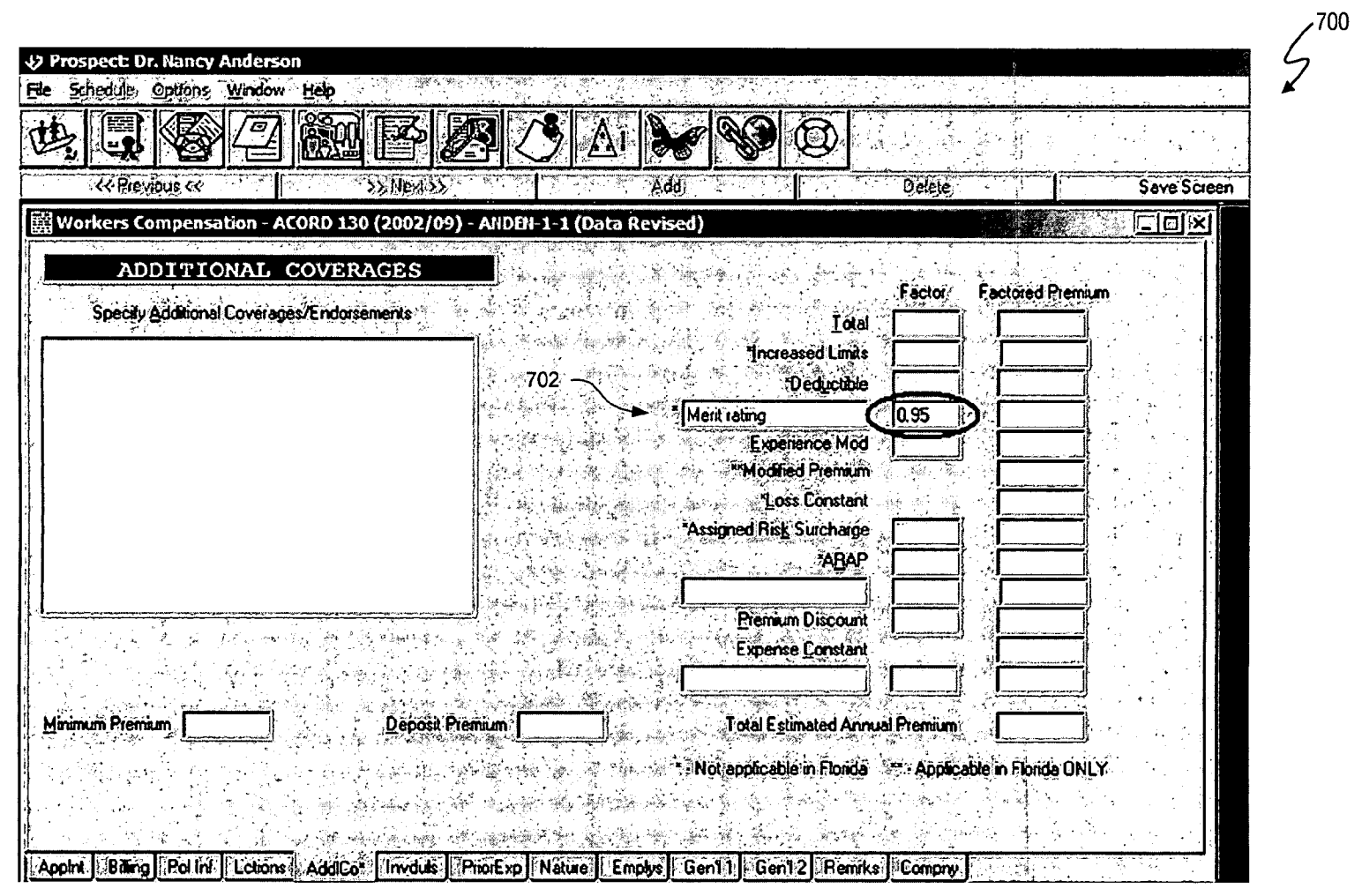

FIG. 7 depicts an example web page, user interface 700 from which a digital information set is generated. In one embodiment, the proxy data analytical process module 404 has replaced the inaccurate, user entered data 702 of "mreit rating" with "merit rating". In another embodiment, the user of a submitter data processing system 302(*i*) has not included a "merit rating". From the context of the digital information set based upon, for example, a parameter associated with the digital information set generated from user interface 700 that indicates the intended recipient of the digital information set or the type of intended recipient, such as an insurance carrier, proxy data analytical process module 404 can determine that a "merit rating" is required but has not been included. The proxy data analytical process module 404 can insert "merit rating" into the digital information set and insert a proxy data value of 0.95 based upon evaluation of other parameters in the digital information set and/or based upon a neutral value to the intended recipient data processing system 308(*i*).

In another embodiment, proxy data analytical process module 404 can detect when content of a data field is inconsistent with an expected value. For example, proxy data analytical process module 404 can, in one embodiment, detect the format, size, or other characteristic of a data field and determine whether the characteristic matches an expected characteristic. For example, data in a business code data field may clearly be in a date format and data in an adjacent date field may be in a business code format. The proxy data analytical process module 404 could detect the data type errors and apply a rule to swap the date and business code data. The proxy data analytical process module 404 could also apply an artificial intelligence processes based on feedback from, for example, recipient data processing systems 308 and or submitter data processing systems 302 to improve determination of appropriate proxy data. Additionally, the proxy data analytical process module 404 can use a heuristic evaluation, such as mapping technology, to provide proxy data when content inconsistent with an expected value is detected or when missing data is detected. For example, in an employee occupation field, a user may have inserted "clerical". However, the intended recipient may expect a code value. The proxy data analytical process module 404, in one embodiment, includes an occupation description-to-occupation code mapping and can insert the appropriate proxy data value for "clerical". If the occupation field is empty, i.e. contains a null value, the proxy data analytical process module 404 could determine a value for the field by searching other parameters in the digital information set, such as a description field that might contain the occupation of a subject of the digital information set.

The proxy data analytical process module 404 can also determine if data fields expected by a recipient data processing system 308(*i*) are missing, insert missing data fields, and include determined, appropriate proxy data. The proxy data sent to the recipient data processing system 308(*i*) can be tailored to the specific recipient data processing system, i.e. one system might need an X data field and another system might not need the X data field but might need a Y data field, and so on.

Once proxy data analytical process module 404 determines the appropriate proxy data for a candidate field, in operation 514 proxy data analytical process module 404 modifies the data field to include the determined proxy data. The proxy data analytical process module 404 can be programmed to adapt to virtually any type of DIS 304(*i*) and apply virtually any rule or other logic to determine appropriate proxy data.

The electronic form handler 406 is a module that performs one embodiment of operation 516 and sends the proxy data augmented DIS 304(*i*) to its intended recipient using the appropriate transmission protocols. The identification of proxy data used module 406 can, for example, insert information into the DIS 304(*i*) to identify data fields that include proxy data. The identification of proxy data used module 406 can also, for example, inform the submitter data processing system 302(*i*) and/or intended recipient data processing system(s) 308 that proxy data was included in the DIS 304(*i*) and identify the proxy data used. Other processes can be associated with the identification process such as a process to prevent a submitter data processing system 302 from accepting a quote from a recipient data processing system 308 until the proxy data is replaced with actual data. In some embodiments, the process can also delete information provided to a recipient data processing system 308(*i*) once the recipient data processing system 308(*i*) reviews the information to prevent the information from permanently residing on the intended recipient data processing system 308(*i*).

Operation 518 identifies proxy data used to augment a digital information set, and prompts the originator of the digital information set to replace the proxy data with actual data or indicate that the proxy data represents actual data. FIG. 8 depicts a digital information set 800 that reports occurrences of proxy data and incomplete data in various digital information sets to the originator of the digital information set 800. For example, the digital information sets 802 through 816, which represent one embodiment of digital information sets, identified in FIG. 8 were submitted by an insurance agent. The insurance risks represented in each digital information set were matched with one or more insurance carriers. However, documents 802, 812, and 816 included proxy data for missing data. The reference to Agency RADAR refers to a report prepared by an Agency RADAR system. The Agency RADAR system represents an embodiment of data processing system 312 available from Trilogy Software, Inc. of Austin, Tex.

In one embodiment, operation 518 notifies the originator of the digital information sets that proxy data was used and identifies the proxy data used to augment the modified digital information sets. For example, in document 802, proxy data augmentation application 400 determined that the experience modifier and total number of employees at the relevant location were missing and inserted proxy data of 1.0 and 10, respectively. In document 812, proxy data augmentation application 400 determined that the experience modifier and total number of employees at the relevant location were missing and inserted proxy data of 1.0 and 1, respectively. In document 812, proxy data augmentation application 400 determined that the experience modifier, total number of employees, and years in business were missing and inserted proxy data of 1.0, 2, and 5, respectively. Additionally, digital information set 808 was submitted with missing Experience Modifier, Risk Number of Employees, and Risk Remuneration data. The proxy data augmentation application 400 did not insert proxy data for the missing data in digital information set 800 because the proxy data analytical process module 404 did not determine appropriate data to be entered. The remaining digital information sets were submitted with sufficient actual data so that augmentation with proxy data was unnecessary.

In operation 520, once the proxy data is replaced with actual data or confirmed as actual data, the submitter data processing system 302(i) can resubmit the document to the recipient data processing system 308(i). Additionally, if a proxy data augmented digital information set is rejected by an intended recipient, proxy data augmentation application 400 can iterate over the proxy data until the intended recipient accepts the digital information set or until it is determined that any further iterations of the proxy data would be undesirable (e.g. the proxy data would be outside of a set of predetermined boundary values and/or it is determined that the digital information set is being rejected for reasons other than the content of proxy data). The increments of iterated proxy data is a matter of design choice.

Thus, the proxy data augmentation system 300 and intelligent proxy augmentation process 500 can significantly improve digital information set generation and review efficiency by automatically determining proxy data for candidate fields using analytical processes that utilize contextual information and one or more parameters associated with the digital information set. Digital information sets can, therefore, be submitted without conducting manual research and without guessing by individuals. The submitted digital information sets can be evaluated in a timelier manner without rejection, and, if the actual data closely matches the proxy data, the evaluation of the document recipient will be validated.

Figure 9:
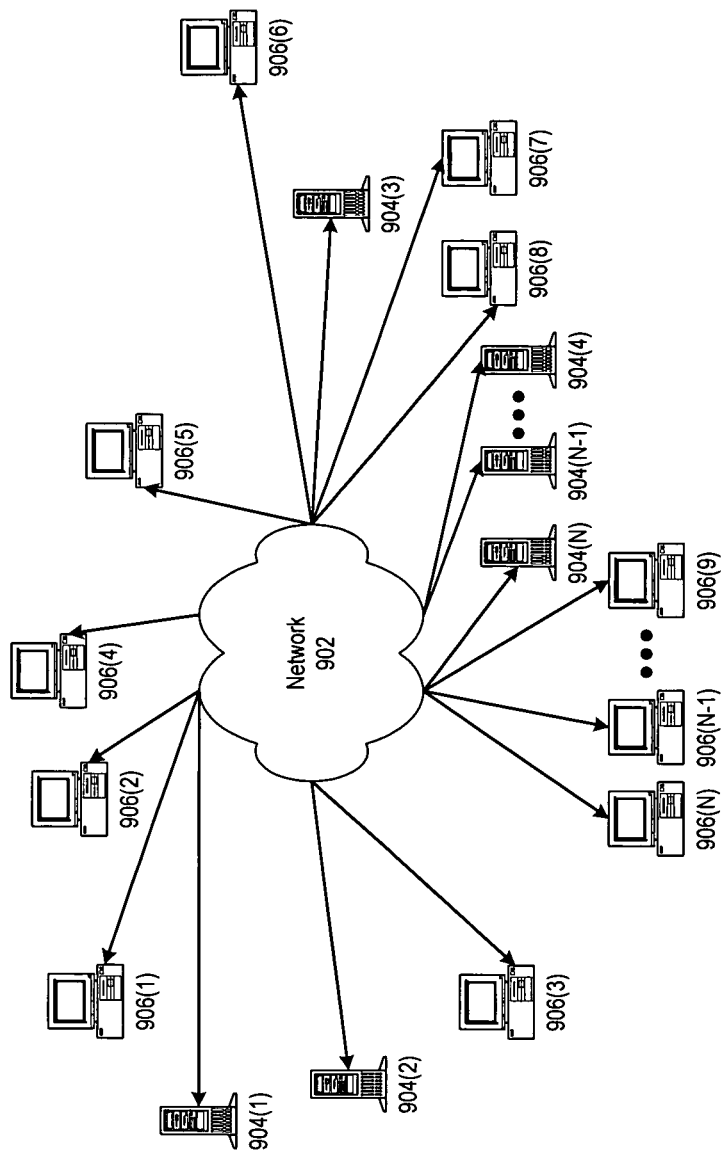
FIG. 9 depicts a block diagram illustrating a network environment in which an automated matching system and process may be practiced.

FIG. 9 is a block diagram illustrating a network environment in which a proxy data augmentation system 300 and intelligent proxy augmentation process 500 may be practiced. Network 902 (e.g. a private wide area network (WAN) or the Internet) includes a number of networked server data processing systems 904(1)-(N) that are accessible by client data processing systems 906(1)-(N), where N is the number of server data processing systems connected to the network. Communication between client data processing systems 906(1)-(N) and server data processing systems 904(1)-(N) typically occurs over a network, such as a public switched telephone network over asynchronous digital subscriber line (ADSL) telephone lines or high-bandwidth trunks, for example communications channels providing T1 or OC3 service. Client data processing systems 906(1)-(N) typically access server data processing systems 904(1)-(N) through a service provider, such as an internet service provider ("ISP") by executing application specific software to as a browser, on one of client data processing systems 906(1)-(N).

Client data processing systems 906(1)-(N) and/or server data processing systems 904(1)-(N) may be, for example, data processing systems of any appropriate design, including a mainframe, a mini-computer, a personal data processing system including notebook computers, a wireless, mobile computing device (including personal digital assistants). These data processing systems are typically information handling systems, which are designed to provide computing power to one or more users, either locally or remotely. Such a data processing system may also include one or a plurality of input/output ("I/O") devices coupled to the system processor to perform specialized functions. Mass storage devices such as hard disks, compact disk ("CD") drives, digital versatile disk ("DVD") drives, and magneto-optical drives may also be provided, either as an integrated or peripheral device. One such example data processing system is shown in detail in FIG. 10.

Figure 10:
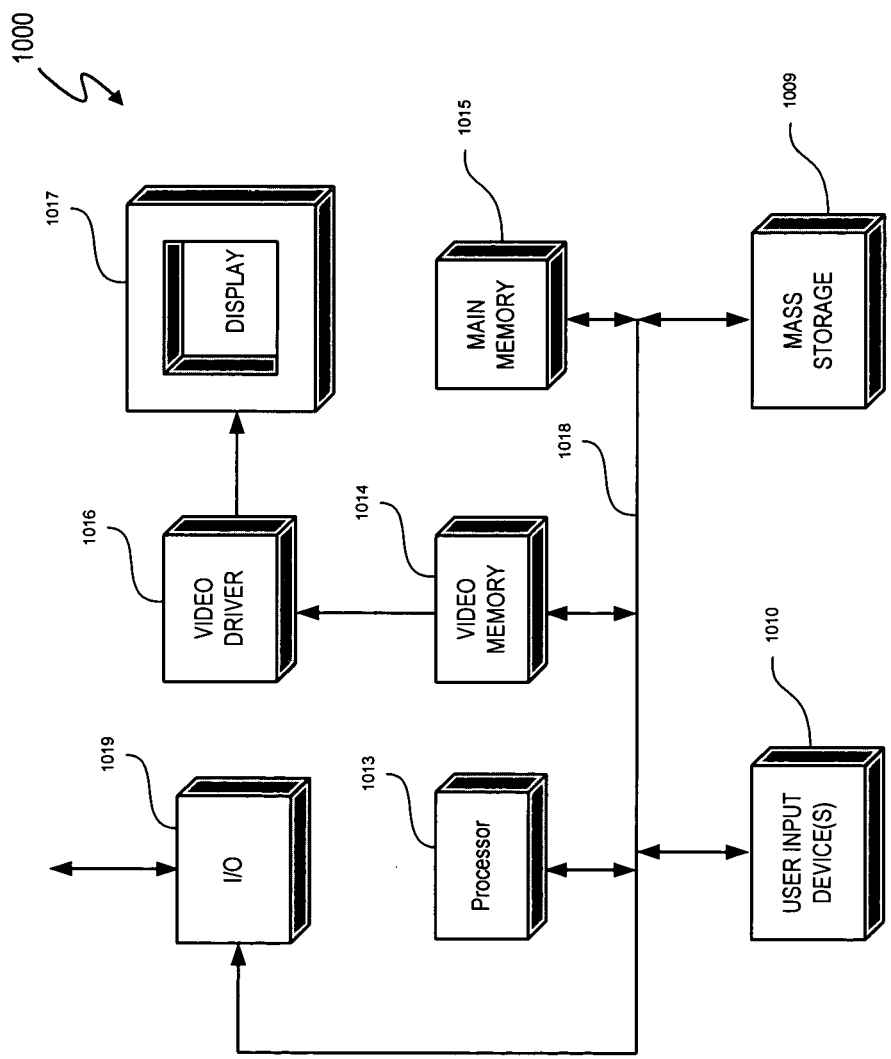
FIG. 10 depicts an example data processing system used in the network of FIG. 9.

Embodiments of the proxy data augmentation system 300 and intelligent proxy augmentation process 500 can be implemented on a data processing system such as a general-purpose computer 1000 illustrated in FIG. 10. Input user device(s) 1010, such as a keyboard and/or mouse, are coupled to a bi-directional system bus 1018. The input user device(s) 1010 are for introducing user input to the data processing system and communicating that user input to processor 149. The data processing system of FIG. 10 generally also includes a video memory 1014, main memory 1015 and mass storage 1009, all coupled to bi-directional system bus 1018 along with input user device(s) 1010 and processor 149. The mass storage 1009 may include both fixed and removable media, such as other available mass storage technology. Bus 1018 may contain, for example, 32 address lines for addressing video memory 1014 or main memory 1015. The system bus 1018 also includes, for example, an n-bit data bus for transferring DATA between and among the modules, such as processor 1013, main memory 1015, video memory 1014 and mass storage 1009, where "n" is, for example, 32 or 64. Alternatively, multiplex data/address lines may be used instead of separate data and address lines.

I/O device(s) 1019 may provide connections to peripheral devices, such as a printer, and may also provide a direct connection to remote server data processing systems via a telephone link or to the Internet via an ISP. I/O device(s) 1019 may also include a network interface device to provide a direct connection to remote server data processing systems via a direct network link to the Internet via a POP (point of presence). Such connection may be made using, for example, wireless techniques, including digital cellular telephone connection, Cellular Digital Packet Data (CDPD) connection, digital satellite data connection or the like. Examples of I/O devices include modems, sound and video devices, and specialized communication devices such as the aforementioned network interface.

Computer programs and data are generally stored as instructions and data in mass storage 1009 until loaded into main memory 1015 for execution. Computer programs may also be in the form of electronic signals modulated in accordance with the computer program and data communication technology when transferred via a network.

The processor 1013, in one embodiment, is a microprocessor manufactured by Intel Corporation of California or Advanced Micro Devices of California. However, any other suitable single or multiple microprocessors or microcomputers may be utilized. Main memory 1015 is, for example, a dynamic random access memory (DRAM). Video memory 1014 is a dual-ported video random access memory. One port of the video memory 1014 is coupled to video amplifier 1016. The video amplifier 1016 is used to drive the display 1017. Video amplifier 1016 is well known in the art and may be implemented by any suitable means. This circuitry converts pixel DATA stored in video memory 1014 to a raster signal suitable for use by display 1017. Display 1017 is a type of monitor suitable for displaying graphic images.

The data processing system described above is for purposes of example only. The proxy data augmentation system 300 and intelligent proxy augmentation process 500 may be implemented in any type of data processing system or programming or processing environment. It is contemplated that the proxy data augmentation system 300 and intelligent proxy augmentation process 500 might be run on a stand-alone data processing system, such as the one described above. The proxy data augmentation system 300 and intelligent proxy augmentation process 500 might also be run from a server data processing systems system that can be accessed by a plurality of client data processing systems interconnected over an intranet network. Finally, the proxy data augmentation system 300 and intelligent proxy augmentation process 500 may be run from a server data processing system that is accessible to clients over the Internet.

Although the present invention has been described in detail, it should be understood that various changes, substitutions and alterations can be made hereto without departing from the spirit and scope of the invention as defined by the appended claims.

What is claimed is:

1. A data processing system that utilizes adapted data fields in a digital information set to automate population of data fields in a digital information set with contextual proxy data using specialized data types, the system comprising:
 a processor; and
 a memory coupled to the processor, the memory having processor executable code embodied therein that when executed transforms the data processing system into a machine for automatically determining and automatically populating data fields with contextual proxy data in a digital information set by causing the processor to:
  receive a digital information set that includes the data fields, wherein each of the data fields includes a data type representing a type of the parameter that the data field is designed to contain and to be determined by an identity of an intended recipient of the digital information set;
  review the digital information set to determine an identity of an intended recipient of the digital information set;
  determine a context of each data field from the data type of the data field and the identity of the intended recipient of the digital information set;
  identify each data field of the received digital information set whose content is a candidate for proxy data by determining if the content is incomplete, empty, or, based on the determined context of the data field, contains information that does not comply with rules that allow the processor to determine at least one of accuracy and relevancy;
  evaluate the data type and the determined context of each of the data fields and determine proxy data that correlates with the data type and the context of each data field with which to populate each data field;
  modify the digital information set with the determined proxy data; and
  transmit the digital information set modified with the determined proxy data to a recipient electronic system.

2. The system of claim 1 wherein the content of the field in the digital information set is a candidate for proxy data when the content is empty.

3. The system of claim 1 wherein the content of the field in the digital information set is a candidate for proxy data when the content is not consistent with an expected characteristic, wherein the characteristic is a member of a group consisting of data format, data value, data size, or data type.

4. The system of claim 1 wherein the code to cause the processor to modify the digital information set with proxy data determined by the process comprises code to:
 populate the field with the appropriate proxy data determined by the process.

5. The system of claim 1 wherein the code to cause the processor to modify the digital information set with proxy data determined by the process comprises code selected from a group consisting of code to augment existing data in the digital information set with additional data, code to revise the existing data, or code to replace the existing data.

6. The system of claim 1 wherein the memory further comprises processor executable code embodied therein to cause the processor to:
 determine a most likely default value for the data field based on review of data in the digital information set that is related to the context of the data field.

7. The system of claim 6 wherein:
 the data field is a "number of employees" field, the data related to the context of the field is "total payroll", "average pay per employee for a particular business class code", and the "business class code"; and
 to determine a most likely proxy value for the data field comprises solving "number of employees=(Total Payroll)/(Estimated Average pay per employee)" for the "number of employees".

8. The system of claim 6 wherein the proxy value is a neutral value for the intended recipient of the digital information set.

9. The system of claim 1 wherein the process is comprised of processor executable code stored in the memory to interpret data populating the data field and determine one or more most likely interpretations of the data populating the data field that correspond to data acceptable to the intended recipient of the digital information set.

10. The system of claim 1 wherein the memory further comprises processor executable code embodied therein to cause the processor to:
 perform a heuristic evaluation of the at least one other parameter in the digital information set to determine appropriate proxy data with which to populate the data field.

11. The system of claim 1 wherein the memory further comprises processor executable code embodied therein to cause the processor to:
 indicate the proxy data used to modify the digital information set.

12. The system of claim 1 wherein the memory further comprises processor executable code embodied therein to cause the processor to:
 send the digital information set modified with the proxy data to the intended recipient.

13. The system of claim 12 wherein the memory further comprises processor executable code embodied therein to cause the processor to:
 iterate the content of the proxy data;
 modify the digital information set with iterated proxy data; and
 resend the digital information set with the iterated proxy data.

14. The system of claim 12 wherein the code to send the digital information set modified with the proxy data to the intended recipient further comprises code to send the digital information set modified with the proxy data to the intended recipient to obtain a quote from an insurance carrier.

15. The system of claim 12 wherein the memory further comprises processor executable code embodied therein to cause the processor to:
 inform an intended recipient that the digital information set includes proxy data.

16. The system of claim 15 wherein the memory further comprises processor executable code embodied therein to cause the processor to identify the proxy data included in the digital information set.

17. The system of claim 12 wherein the memory further comprises processor executable code embodied therein to cause the processor to:
inform an originator of the digital information set that the digital information set includes proxy data.

18. The system of claim 17 wherein the memory further comprises processor executable code embodied therein to cause the processor to identify the proxy data included in the digital information set.

19. The system of claim 1 wherein the memory further comprises processor executable code embodied therein to cause the processor to:
prompt a user of the data processing system to provide actual data to substitute for proxy data.

20. The system of claim 1 wherein the memory further comprises processor executable code embodied therein to cause the processor to:
inform a user of the data processing system that the digital information set includes proxy data.

21. The system of claim 1 wherein the memory further comprises processor executable code embodied therein to cause the processor to:
prompt a user of the data processing system to verify accuracy of the proxy data.

22. The system of claim 1 wherein the digital information set comprises an identification of an insurance risk.

23. The system of claim 1 wherein the digital information set comprises a request to receive a response from an insurance carrier wherein a type of response requested is selected from a group consisting of a non-bindable quote, a bindable quote, or an indication if an insurance risk matches the type of risk for which an insurance carrier desires to underwrite.

24. The system of claim 1 wherein at least one parameter is data representing the intended recipient of the digital information set.

25. The system of claim 1 wherein at least one parameter is data representing a preference of the intended recipient of the digital information set.

26. The system of claim 1 wherein the digital information set is derived from a digital information set received from a submitter data processing system.

27. The system of claim 1 wherein the proxy data is determined from requirements of the intended recipient of the digital information set.

28. The system of claim 1 wherein the field associated with the digital information set is a field that is missing in the digital information set but is expected by the intended recipient of the digital information to exist.

29. A non-transitory, computer readable program product having processor executable code embodied therein to cause a processor to utilize adapted data fields in a digital information set to automate population of data fields in a digital information set with contextual proxy data using specialized data types and transform a computer system into a machine to:
receive a digital information set that includes data fields, wherein each of the data fields includes a data type representing a type of the parameter that the data field is designed to contain and to be determined by an identity of an intended recipient of a digital information set;
review the digital information set to determine an identity of an intended recipient of the digital information set;
determine a context of each data field from the data type of the data field and the identity of the intended recipient of the digital information set;
identify each data field of the received digital information set whose content is a candidate for proxy data by determining if the content is incomplete, empty, or, based on the determined context of the data field, contains information that does not comply with rules that allow the processor to determine at least one of accuracy and relevancy;
evaluate the data type and the determined context of each of the data fields and determine proxy data that correlates with the data type and the context of each data field with which to populate each data field;
modify the digital information set with the determined proxy data; and
transmit the digital information set modified with the determined proxy data to a recipient electronic system.

30. The computer readable program product of claim 29 wherein the content of the field in the digital information set is a candidate for proxy data when the content is empty.

31. The computer readable program product of claim 29 wherein the content of the field in the digital information set is a candidate for proxy data when the content is not consistent with an expected characteristic, wherein the characteristic is a member of a group consisting of data format, data value, data size, or data type.

32. The computer readable program product of claim 29 wherein the code to cause the processor to modify the digital information set with proxy data determined by the process comprises code to:
populate the field with the appropriate proxy data determined by the process.

33. The computer readable program product of claim 29 wherein the code to cause the processor to modify the digital information set with proxy data determined by the process comprises code selected from a group consisting of code to augment existing data in the digital information set with additional data, code to revise the existing data, or code to replace the existing data.

34. The computer readable program product of claim 29 wherein the computer readable program product further comprises processor executable code embodied therein to cause the processor to:
determine a most likely default value for the data field based on review of data in the digital information set that is related to the context of the data field.

35. The computer readable program product of claim 34 wherein:
the data field is a "number of employees" field, the data related to the context of the field is "total payroll", "average pay per employee for a particular business class code", and the "business class code"; and
to determine a most likely proxy value for the data field comprises solving "number of employees=(Total Payroll)/(Estimated Average pay per employee)" for the "number of employees".

36. The computer readable program product of claim 34 wherein the proxy value is a neutral value for the intended recipient of the digital information set.

37. The computer readable program product of claim 29 wherein the process is comprised of processor executable code embodied in the computer readable program product to interpret data populating the field and determine one or more most likely interpretations of the data populating the field that correspond to data acceptable to the intended recipient of the digital information set.

38. The computer readable program product of claim 29 wherein the computer readable program product further comprises processor executable code embodied therein to cause the processor to:
perform a heuristic evaluation of the at least one other parameter in the digital information set to determine appropriate proxy data with which to populate the data field.

39. The computer readable program product of claim 29 wherein the computer readable program product further comprises processor executable code embodied therein to cause the processor to:
indicate the proxy data used to modify the digital information set.

40. The computer readable program product of claim 29 wherein the computer readable program product further comprises processor executable code embodied therein to cause the processor to:
send the digital information set modified with the proxy data to the intended recipient.

41. The computer readable program product of claim 29 wherein the computer readable program product further comprises processor executable code embodied therein to cause the processor to:
iterate the content of the proxy data;
modify the digital information set with iterated proxy data; and
resend the digital information set with the iterated proxy data.

42. The computer readable program product of claim 29 wherein the code to send the digital information set modified with the proxy data to the intended recipient further comprises code to send the digital information set modified with the proxy data to the intended recipient to obtain a quote from an insurance carrier.

43. The computer readable program product of claim 29 wherein the computer readable program product further comprises processor executable code embodied therein to cause the processor to:
inform the intended recipient that the digital information set includes proxy data.

44. The computer readable program product of claim 29 wherein the computer readable program product further comprises processor executable code embodied therein to cause the processor to identify the proxy data included in the digital information set.

45. The computer readable program product of claim 29 wherein the computer readable program product further comprises processor executable code embodied therein to cause the processor to:
inform an originator of the digital information set that the digital information set includes proxy data.

46. The computer readable program product of claim 45 wherein the computer readable program product further comprises processor executable code embodied therein to cause the processor to identify the proxy data included in the digital information set.

47. The computer readable program product of claim 29 wherein the computer readable program product further comprises processor executable code embodied therein to cause the processor to:
prompt a user of a data processing system to provide actual data to substitute for proxy data.

48. The computer readable program product of claim 29 wherein the computer readable program product further comprises processor executable code embodied therein to cause the processor to:
inform a user of a data processing system that the digital information set includes proxy data.

49. The computer readable program product of claim 29 wherein the computer readable program product further comprises processor executable code embodied therein to cause the processor to:
prompt a user of a data processing system to verify accuracy of the proxy data.

50. The computer readable program product of claim 29 wherein the digital information set comprises an identification of an insurance risk.

51. The computer readable program product of claim 29 wherein the digital information set comprises a request to receive a response from an insurance carrier wherein a type of response requested is selected from a group consisting of a non-bindable quote, a bindable quote, or an indication if an insurance risk matches the type of risk for which an insurance carrier desires to underwrite.

52. The computer readable program product of claim 29 wherein at least one parameter is data representing the intended recipient of the digital information set.

53. The computer readable program product of claim 29 wherein at least one parameter is data representing a preference of the intended recipient of the digital information set.

54. The computer readable program product of claim 29 wherein the digital information set is derived from a digital information set received from a submitter data processing system.

55. The computer readable program product of claim 29 wherein the proxy data is determined from requirements of the intended recipient of the digital information set.

56. The computer readable program product of claim 29 wherein the field associated with the digital information set is a field that is missing in the digital information set but is expected by the intended recipient of the digital information to exist.

57. A method for utilizing adapted data fields in a digital information set to automate population of data fields in a digital information set with contextual proxy data using specialized data types, the method comprising executing an application in a data processing system that transforms the data processing system into a machine for:
receiving a digital information set that includes the data fields, wherein each of the data fields includes a data type representing a type of the parameter that the data field is designed to contain and to be determined by an identity of an intended recipient of the digital information set;
reviewing the digital information set to determine an identity of an intended recipient of the digital information set;
determining a context of each data field from the data type of the data field and the identity of the intended recipient of the digital information set;
identifying each data field of the received digital information set whose content is a candidate for proxy data by determining if the content is incomplete, empty, or, based on the determined context of the data field, contains information that does not comply with rules that allow the processor to determine at least one of accuracy and relevancy;

evaluating the data type and the determined context of each of the data fields and determine proxy data that correlates with the data type and the context of each data field with which to populate each data field;

modifying the digital information set with the determined proxy data; and transmitting the digital information set modified with the determined proxy data to a recipient electronic system.

58. The method of claim 57 wherein the content of the field in the digital information set is a candidate for proxy data when the content is empty.

59. The method of claim 57 wherein the content of the field in the digital information set is a candidate for proxy data when the content is not consistent with an expected characteristic, wherein the characteristic is a member of a group consisting of data format, data value, data size, or data type.

60. The method of claim 57 wherein modifying the digital information set with proxy data determined by the process comprises:

populating the field with the appropriate proxy data determined by the process.

61. The method of claim 57 wherein modifying the digital information set with proxy data determined by the process comprises:

augmenting existing data in the digital information set with additional data;

revising the existing data; and replacing the existing data.

62. The method of claim 57 wherein modifying the digital information set with proxy data determined by the process comprises:

revising the existing data.

63. The method of claim 57 wherein modifying the digital information set with proxy data determined by the process comprises:

replacing the existing data.

64. The method of claim 57 further comprising:

determining a most likely default value for the data field based on review of data in the digital information set that is related to the context of the data field.

65. The method of claim 64 wherein:

the data field is a "number of employees" field, the data related to the context of the field is "total payroll", "average pay per employee for a particular business class code", and the "business class code"; and to determine a most likely proxy value for the data field comprises solving "number of employees=(Total Payroll)/(Estimated Average pay per employee)" for the "number of employees".

66. The method of claim 64 wherein the proxy value is a neutral value for the intended recipient of the digital information set.

67. The method of claim 57 wherein evaluating the data type and the determined context of each of the data fields further comprises interpreting data populating the data field and determining one or more most likely interpretations of the data populating the data field that correspond to data acceptable to the intended recipient of the digital information set.

68. The method of claim 57 further comprising executing an application in the data processing system for:

performing a heuristic evaluation of the at least one other parameter in the digital information set to determine appropriate proxy data with which to populate the data field.

69. The method of claim 57 further comprising executing an application in the data processing system for:

indicating the proxy data used to modify the digital information set.

70. The method of claim 57 further comprising executing an application in the data processing system for:

sending the digital information set modified with the proxy data to the intended recipient.

71. The method of claim 70 further comprising executing an application in the data processing system for:

iterating the content of the proxy data;

modifying the digital information set with iterated proxy data; and resending the digital information set with the iterated proxy data.

72. The method of claim 70 wherein sending the digital information set modified with the proxy data to the intended recipient further comprises sending the digital information set modified with the proxy data to the intended recipient to obtain a quote from an insurance carrier.

73. The method of claim 70 further comprising executing an application in the data processing system for:

informing the intended recipient that the digital information set includes proxy data.

74. The method of claim 73 further comprising executing an application in the data processing system for:

identifying the proxy data included in the digital information set.

75. The method of claim 70 further comprising executing an application in the data processing system for:

informing an originator of the digital information set that the digital information set includes proxy data.

76. The method of claim 75 further comprising executing an application in the data processing system for:

identifying the proxy data included in the digital information set.

77. The method of claim 57 further comprising executing an application in the data processing system for:

prompting a user of the data processing system to provide actual data to substitute for proxy data.

78. The method of claim 57 further comprising executing an application in the data processing system for:

informing a user of the data processing system that the digital information set includes proxy data.

79. The method of claim 57 further comprising executing an application in the data processing system for:

prompting a user of the data processing system to verify accuracy of the proxy data.

80. The method of claim 57 wherein the digital information set comprises an identification of an insurance risk.

81. The method of claim 57 wherein the digital information set comprises a request to receive a response from an insurance carrier wherein a type of response requested is selected from a group consisting of a non-bindable quote, a bindable quote, or an indication if an insurance risk matches the type of risk for which an insurance carrier desires to underwrite.

82. The method of claim 57 wherein at least one parameter is data representing the intended recipient of the digital information set.

83. The method of claim 57 wherein at least one parameter is data representing a preference of the intended recipient of the digital information set.

84. The method of claim 57 wherein the digital information set is derived from a digital information set received from a submitter data processing system.

85. The method of claim 57 wherein the proxy data is determined from requirements of the intended recipient of the digital information set.

86. The method of claim 57 wherein the field associated with the digital information set is a field that is missing in the digital information set but is expected by the intended recipient of the digital information to exist.

* * * * *